(12) United States Patent
Burk et al.

(10) Patent No.: US 6,891,059 B2
(45) Date of Patent: May 10, 2005

(54) ASYMMETRIC SYNTHESIS OF PREGABALIN

(75) Inventors: Mark Joseph Burk, Landbeach (GB); Om Prakash Goel, Ann Arbor, MI (US); Marvin Simon Hoekstra, Holland, MI (US); Thomas Frederick Mich, Ann Arbor, MI (US); Thomas Mulhern, Hudsonville, MI (US); James A. Ramsden, Cambridge (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/182,656

(22) PCT Filed: Jan. 11, 2001

(86) PCT No.: PCT/IB01/00024
§ 371 (c)(1),
(2), (4) Date: Mar. 7, 2003

(87) PCT Pub. No.: WO01/55090
PCT Pub. Date: Aug. 2, 2001

(65) Prior Publication Data
US 2003/0212290 A1 Nov. 13, 2003

Related U.S. Application Data

(60) Provisional application No. 60/190,427, filed on Mar. 17, 2000, and provisional application No. 60/178,359, filed on Jan. 27, 2000.

(51) Int. Cl.$^7$ ............................................. C07C 255/03
(52) U.S. Cl. ...................................................... 558/441
(58) Field of Search ........................................ 558/441

(56) References Cited

U.S. PATENT DOCUMENTS

| | | |
|---|---|---|
| 4,939,288 A | 7/1990 | Talley |
| 5,171,892 A | 12/1992 | Burk |
| 5,532,395 A | 7/1996 | Burk |
| 5,563,175 A | 10/1996 | Silverman et al. |
| 5,616,793 A | 4/1997 | Huckabee et al. |
| 5,629,447 A | 5/1997 | Huckabee et al. |
| 5,637,767 A | 6/1997 | Grote et al. |
| 5,840,956 A | 11/1998 | Grote et al. |
| 6,001,876 A | 12/1999 | Singh et a |
| 6,127,418 A | 10/2000 | Guglietta et al. |

FOREIGN PATENT DOCUMENTS

| | | |
|---|---|---|
| EP | 0380463 | 8/1990 |
| WO | 9638405 | 12/1996 |
| WO | 9640617 | 12/1996 |
| WO | WO 99/31041 | 6/1999 |
| WO | WO 99/52852 | 10/1999 |

OTHER PUBLICATIONS

PCT Internatinal Search Report, PCT/IB01/00024.
Lin et al., "Chiral HPLC Separations for Process Development of S–(+)–isobutyl GABA, a Potential Anti–Epileptic Agent", *J. Liq. Chrom. & Rel. Technol.*, vol. 19, No. 16, 1996, pp. 2699–2708.
Serfass and Casara, "General Synthesis of 3–Substituted Alkenyl GABA as Potential Anticonvulsants", *Bioorganic & Medicinial Chemistry Letters*, vol. 8, 1998, pp. 2599–2602.
Hoekstra et al., "Chemical Development of C1–1008, an Enantiomerically Pure Antoconvulsant", *Organic Process Research & Development*, vol. 1, 1997, pp. 26–38.
Andruszkiewicz, et al., "A Convenient Synthesis of 3–Alkyl–4–aminobutanoic Acids", Synthesis, 1989, p. 953.
Burk, et al., "Asymmetric Catalytic Synthesis of Beta–Branched Amino Acids via Highly Enantioselective Hydrogenation Reactions", J. Am. Chem. Soc., 1995, vol. 117, pp. 9375–9376.
Yamamoto, et al., Bull. Chem. Soc. Jap., 1985, vol. 58, p. 3397.
Yen et al., "Enantioselective synthesis of PD144723: A potent sterospecific anticonvulsant", Bioorganic & Medicinal Chemistry Letters, 1994, vol. 4, p. 823.

*Primary Examiner*—Johann Richter
*Assistant Examiner*—Ebenezer Sackey
(74) *Attorney, Agent, or Firm*—Karen DeBenedictis; Matthew J. Russo

(57) ABSTRACT

This invention provides a method of making (S)-(+)-3-(aminomethyl)-5-methylhexanoic acid (pregabalin) or a salt thereof via an asymmetric hydrogenation synthesis. Pregabalin is useful for the treatment and prevention of seizure disorders, pain, and psychotic disorders. The invention also provides intermediates useful in the production of pregabalin.

26 Claims, No Drawings

ASYMMETRIC SYNTHESIS OF PREGABALIN

FIELD OF THE INVENTION

This application claims priority from U.S. Provisional Patent Application Ser. No. 60/190,427, filed Mar. 17, 2000, and U.S. Provisional Patent Application Ser. No. 60/178,359, filed Jan. 27, 2000.

This invention relates to a method of making (S)-(+)-3-(aminomethyl)-5-methylhexanoic acid (pregabalin) in an asymmetric synthesis. Pregabalin is useful for the treatment and prevention of seizure disorders, pain, and psychotic disorders.

BACKGROUND OF THE INVENTION (S)-(+)-3-(Aminomethyl)-5-methylhexanoic acid is known generically as pregabalin. The compound is also called (S)-(+)-β-isobutyl-γ-aminobutyric acid, (S)-isobutyl-GABA, and CI-1008. Pregabalin is related to the endogenous inhibitory neurotransmitter γ-aminobutyric acid or GABA, which is involved in the regulation of brain neuronal activity. Pregabalin has anti-seizure activity, as described by Silverman et al., U.S. Pat. No. 5,563,175. Other indications for pregabalin are also currently being pursued (see, for example. Guglietta et al., U.S. Pat. No. 6,127,418, and Singh et al., U.S. Pat. No. 6,001,876).

A seizure is defined as excessive unsynchronized neuronal activity that disrupts normal brain function. It is thought that seizures can be controlled by regulating the concentration of the GABA neurotransmitter. When the concentration of GABA diminishes below a threshold level in the brain, seizures result (Karlsson et al., *Biochem. Pharmacol.* 1974:23:3053); when the GABA level rises in the brain during convulsions, the seizures terminate (Havashi. *Physiol.* (London), 1959;145:570).

Because of the importance of GABA as a neurotransmitter, and its effect on convulsive states and other motor dysfunctions, a variety of approaches have been taken to increase the concentration of GABA in the brain. In one approach, compounds that activate L-glutamic acid decarboxylase (GAD) have been used to increase the concentration of GABA, as the concentrations of GAD and GABA vary in parallel, and increased GAD concentrations result in increased GABA concentrations (Janssens de Varebeke et al., *Biochem. Pharmacol.*, 1983;32:2751; Loscher, *Biochem. Pharmacol.*, 1982;31:837; Phillips et al., *Biochem. Pharmacol.*, 1982;31:2257). For example, the racemic compound (±)-3-(aminomethyl)-5-methylhexanoic acid (racemic isobutyl-GABA), which is a GAD activator, has the ability to suppress seizures while avoiding the undesirable side effect of ataxia.

The anticonvulsant effect of racemic isobutyl-GABA is primarily attributable to the S-enantiomer (pregabalin). That is, the S-enantiomer of isobutyl-GABA shows better anticonvulsant activity than the R-enantiomer (see, for example, Yuen et al., *Bioorganic & Medicinal Chemistry Letters*, 1994;4:823). Thus, the commercial utility of pregabalin requires an efficient method for preparing the S-enantiomer substantially free of the R-enantiomer.

Several methods have been used to prepare pregabalin. Typically, the racemic mixture is synthesized and then subsequently resolved into its R- and S-enantiomers (see U.S. Pat. No. 5,563,175 for synthesis via an azide intermediate). Another method uses potentially unstable nitro compounds, including nitromethane, and an intermediate that is reduced to an amine in a potentially exothermic and hazardous reaction. This synthesis also uses lithium bis(trimethylsilylamide) in a reaction that must be carried out at −78° C. (Andruszkiewicz et al., *Synthesis*, 1989:953). More recently, the racemate has been prepared by a "malonate" synthesis, and by a Hofmann synthesis (U.S. Pat. Nos. 5,840,956; 5,637,767; 5,629,447; and 5,616,793). The classical method of resolving a racemate is used to obtain pregabalin according to these methods. Classical resolution involves preparation of a salt with a chiral resolving agent to separate and purify the desired S-enantiomer. This involves significant processing, and also substantial additional cost associated with the resolving agent. Partial recycle of the resolving agent is feasible, but requires additional processing and cost, as well as associated waste generation. Moreover, the undesired R-enantiomer cannot be efficiently recycled and is ultimately discarded as waste. The maximum theoretical yield of pregabalin is thus 50%, since only half of the racemate is the desired product. This reduces the effective throughput of the process (the amount that can be made in a given reactor volume), which is a component of the production cost and capacity.

Pregabalin has been synthesized directly via several different synthetic schemes. One method includes use of n-butyllithium at low temperatures (≦35° C.) under carefully controlled conditions. This synthetic route requires the use of (4R,5S)-4-methyl-5-phenyl-2-oxazolidinone as a chiral auxiliary to introduce the stereochemical configuration desired in the final product (U.S. Pat. No. 5,563,175). Thus, although these general strategies provide the target compound in high enantiomeric purity, they are not practical for large-scale synthesis because they employ costly reagents which are difficult to handle, as well as special cryogenic equipment to reach the required operating temperatures.

Because pregabalin is being developed as a commercial pharmaceutical product, the need exists for an efficient, cost effective, and safe method for its large-scale synthesis. In order to be viable for commercial manufacturing, such a process needs to be highly enantioselective, for example, where the product is formed with a substantial excess of the correct enantiomer. An object of this invention is to provide such a process, namely an asymmetric hydrogenation process.

Asymmetric hydrogenation processes are known for some compounds. Burk et al., in WO 99/31041 and WO 99/52852, describe asymmetric hydrogenation of β-substituted and β,β-disubstituted itaconic acid derivatives to provide enantiomerically enriched 2-substituted succinic acid derivatives. The itaconic substrates possess two carboxyl groups, which provide the requisite steric and electronic configuration to direct the hydrogenation to produce an enriched enantiomer. The disclosures teach that salt forms of the formula RR'C═C (CO$_2$Me)CH$_2$CO$_2$—Y$^+$ are required to obtain hydrogenated products having at least 95% enantiomeric excess.

According to U.S. Pat. No. 4,939,288, asymmetric hydrogenation does not work well on substrates having an isobutyl group. We have now discovered that an isobutyl cyano carboxy acid, salt or ester substrate, of the formula iPrCH═C(CN)CH$_2$CO$_2$R, can be selectively hydrogenated to provide an enantiomerically enriched nitrile derivative, which can be subsequently hydrogenated to produce substantially pure pregabalin. This selectivity is particularly surprising given the dramatic differences in steric configuration and inductive effects of a nitrile moiety compared to a carboxy group. Indeed, there is no teaching in the prior art of the successful asymmetric hydrogenation of any cyano substituted carboxy olefin of this type.

SUMMARY OF THE INVENTION

The present invention provides an efficient method of preparing (S)-3-(aminomethyl)-5-methylhexanoic acid (pregabalin). The method comprises asymmetric hydrogenation of a cyano substituted olefin to produce a cyano precursor of (S)-3-(aminomethyl)-5-methylhexanoic acid. The method further comprises a reaction to convert the cyano intermediate into (S)-3-(aminomethyl)-5-methylhexanoic acid. The asymmetric synthesis of (S)-3-(aminomethyl)-5-methylhexanoic acid described herein results in a substantial enrichment of pregabalin over the undesired (R)-3-(aminomethyl)-5-methylhexanoic acid. The R-enantiomer is produced only as a small percentage of the final product.

The present invention offers several advantages over previous methods of making pregabalin. For example, processing to remove the undesired R-enantiomer and subsequent disposal of this waste is minimized. Because the S-enantiomer is greatly enriched in the final product, the asymmetric approach is more efficient. Furthermore, the present method does not require the use of hazardous nitro compounds, costly chiral auxiliaries, or low temperatures as required in previous methods. Moreover, unlike the classical resolution approaches or the chiral auxiliary route, which require stoichiometric amounts of the chiral agent, this synthesis utilizes sub-stoichiometric quantities of the chiral agent as a catalyst. Thus, the method of the present invention has both economic and environmental advantages.

DETAILED DESCRIPTION OF THE INVENTION

As used herein, the term "lower alkyl" or "alkyl" means a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "aryl" means an aromatic carbocyclic group having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl). The aryl group may be unsubstituted or substituted by 1 to 3 substituents selected from alkyl, O-alkyl and S-alkyl, OH, SH, —CN, halogen, 1,3-dioxolanyl, $CF_3$, $NO_2$, $NH_2$, $NHCH_3$, $N(CH_3)_2$, NHCO-alkyl, —$(CH_2)_m CO_2 H$, —$(CH_2)_m CO_2$-alkyl, —$(CH_2)_m SO_3 H$, —NH alkyl, —N(alkyl)$_2$, —$(CH_2)_m PO_3 H_2$, —$(CH_2)_m PO_3(alkyl)_2$, —$(CH_2)_m SO_2 NH_2$, and —$(CH_2)_m SO_2 NH$-alkyl, wherein alkyl is defined as above and m is 0, 1, 2, or 3. A preferable aryl group of the present invention is phenyl. Typical substituted aryl groups include methylphenyl, 4-methoxybiphenyl, 3-chloronaphth-1-yl, and dimethylaminophenyl.

The term "arylalkyl" means an alkyl moiety (as defined above) substituted with an aryl moiety (also as defined above). Examples include benzyl and 2-naphthlethyl.

The disclosures in this application of all articles and references, including patents, are incorporated herein by reference.

The present invention provides an efficient synthesis of (S)-3-(aminomethyl)-5-methylhexanoic acid (pregabalin). This synthesis is depicted in Scheme 1, below,

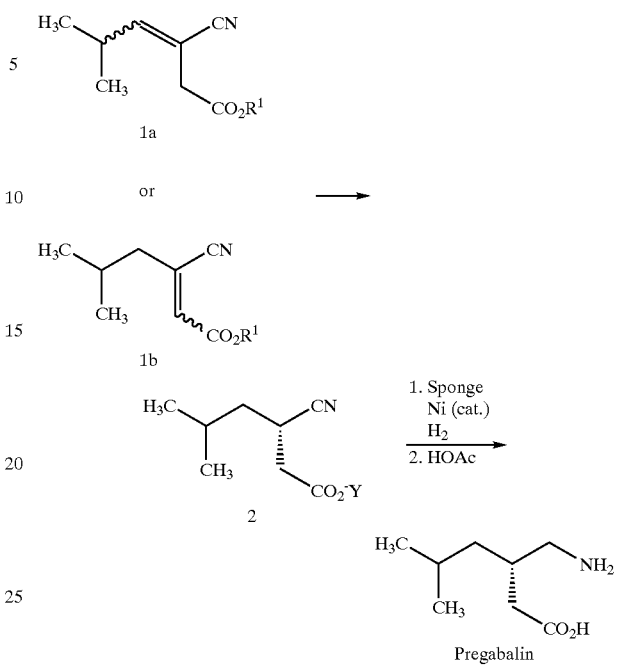

wherein $R^1$ is lower alkyl, aryl, arylalkyl or allyl; and Y is a cation, and preferably $H^+$, the salt of a primary or secondary amine, an alkaline earth metal, such as tert-butyl ammonium, or an alkali metal such as sodium.

As illustrated in Scheme 1, a metal salt 2 (where Y is potassium, for example) of a cyano alkanoic acid may be obtained from the cyano hexenoate ester 1a or 1b by sequential asymmetric hydrogenation and ester hydrolysis to the free acid or salt. Subsequent reduction of the nitrile 2 by routine hydrogenation with a catalyst such as nickel, followed by acidification of the carboxylate salt, affords pregabalin. Alternatively, these steps can be reversed, such that the substrate for asymmetric hydrogenation is the acid or salt 4

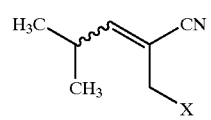

where X is $CO_2 H$ or $CO_2$—Y, and Y is a cation. Compound 4 can exist as the individual E or Z geometric isomer, or a mixture thereof. Salts can be formed by reacting the free acid (X is $CO_2 H$) with a strong base such as a metal hydroxide, e.g., KOH. Alternatively, the salt may be formed with, for example, a counterion $WH+$ such as that derived from an amine (W) or a phosphine (W). Primary $C_{1-10}$ alkylamines and cycloalkylamines are preferred, in particular, tert-butylamine. Tertiary amines such as triethylamine may also be used. Again, subsequent reduction of the nitrile 2 by standard methods, followed by acidification of the carboxylate salt, affords pregabalin.

In the general synthesis of pregabalin according to Scheme 1, the cyano olefin compound 1a or 1b undergoes ester hydrolysis and asymmetric hydrogenation to form the desired enantiomer of a 3-cyano-5-methylhexanoic acid or the corresponding carboxylate salt 2. The olefin substrate can be the individual E or Z geometric isomer, or a mixture thereof. Subsequent reduction of the nitrile 2, followed by acidification of the carboxylate salt, affords pregabalin.

The asymmetric hydrogenation step is performed in the presence of a chiral catalyst, preferably a rhodium complex of an (R,R)-DuPHOS or (S,S)-DuPHOS ligand, commercially available from Strem Chemicals, Inc. (7 Mulliken Way, Newburyport, Mass. 01950-4098) and Chirotech Technology Limited (Cambridge Science Park, Cambridge, Great Britain) (see U.S. Pat. Nos. 5,532,395 and 5,171,892). The ligand preferably has the formula

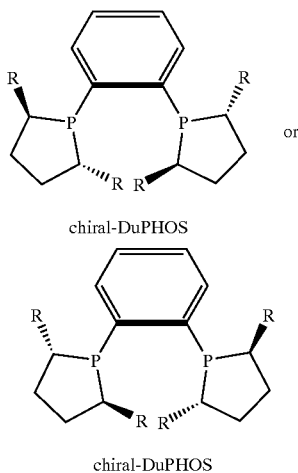

chiral-DuPHOS wherein R is lower alkyl. Preferred alkyl groups for R are n-alkyl groups, such as, for example, methyl, ethyl, propyl, butyl, pentyl or hexyl. More preferred alkyl groups for R are methyl or ethyl. Other catalysts that can be used include rhodium complexes of chiral-BPE and chiral-DIPAMP which have the formulas

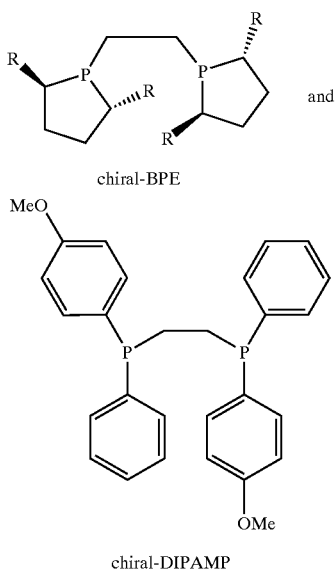

Such catalysts generally are complexed with 1,5-cyclooctadiene (COD). These agents are fully described by Burk et al. in *J. Am. Chem. Soc.*, 1995;117:9375.

The asymmetric hydrogenation reaction is carried out under a hydrogen atmosphere and preferably in a protic solvent such as methanol, ethanol, isopropanol, or a mixture of such alcohols with water.

The cyano hexenoate starting materials (e.g., 1a) are readily available (Yamamoto et al., *Bull. Chem. Soc. Jap.*, 1985;58:3397). They can be prepared according to Scheme 2, below,

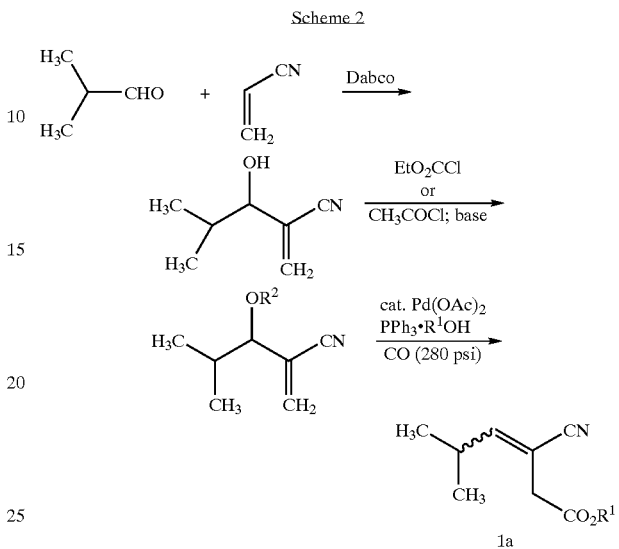

wherein $R^1$ is as defined above in Scheme 1 and $R^2$ is $COCH_3$ or $CO_2$alkyl.

In the synthesis of a compound 1a according to Scheme 2, amine catalyzed addition of acrylonitrile (i.e., the Baylis-Hillman reaction) to 2-methylpropanal affords the cyano allylic alcohol. Typical amines used to catalyze the condensation include agents such as 1,4-diazabicyclo[2,2,2]octane (Dabco). The cyano allylic alcohol is subsequently converted to either an alkyl carbonate (e.g., by reaction with an alkyl halo formate such as ethyl chloro formate) or the respective acetate (by reaction with acetic anhydride or acetyl chloride). The resulting 2-(2-methylpropyl)prop-2-enenitrile is then subjected to palladium-catalyzed carbonylation to produce ethyl 3-cyano-5-methylhex-3-enoate 1a (e.g., where $R^1$ is methyl or ethyl).

In one embodiment of the invention illustrated in Scheme 3 below, asymmetric hydrogenation is first carried out on 1a (where $R^1$ is ethyl for example) to form the (S)-3-cyano-5-ethylhexanoic acid ester 3. Use of chiral (S,S) hydrogenation catalysts from the bisphospholane series, for example [(S,S)-Me-DuPHOS]Rh(COD)$^+$BF$_4^-$ on the ester substrates (e.g., $R^1$ is alkyl) provides products enriched in the desired S-enantiomer. The ester 3 is subsequently hydrolyzed to the acid or salt 2. Scheme 3 below shows this synthetic route. wherein Y is as defined above for Scheme 1. By switching to the catalyst [(R,R)-Me-DuPHOS]Rh(COD)$^+$BF$_4^-$, the hydrogenation product is enriched in (R)-3-cyano-5-methylhexanoic acid ethyl ester. Typically, these hydrogenation processes provide for substrate conversion of at least 90%, and enantiomeric enrichment (e.e.) of 20% to 25%. Further enrichment of the product can be effected by selective recrystallization with a chiral resolving agent, as described below.

Scheme 3

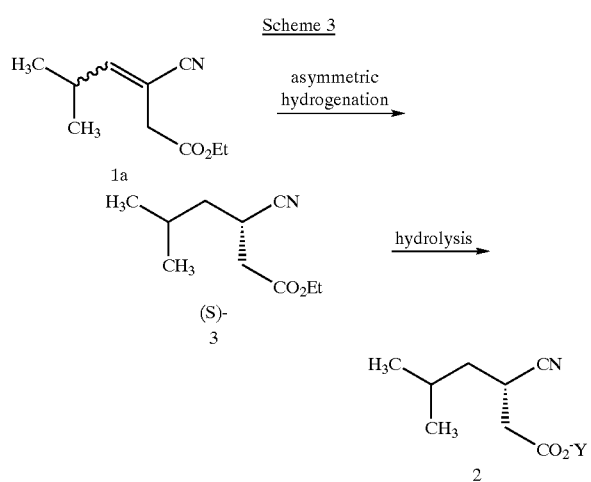

A preferred embodiment of the invention is illustrated in Scheme 4, where the ester 1a is first hydrolyzed to the salt of the 3-hexenoic acid 4, (e.g., 4a as shown in Scheme 4 where Y is sodium or potassium). The cyano hexanoic acid salt 4a is then hydrogenated to the salt 2. The cyano hexanoic acid salt 4a may be isolated, or may be prepared in situ prior to hydrogenation. Scheme 4 below depicts this preferred embodiment, wherein Y is as defined above for Scheme 1. A distinctive feature of the hydrogenation of the salt 4a is that the desired S-enantiomer 2 is obtained by use of a chiral (R,R) catalyst from the bisphospholane series, for example [(R,R)-Me-DuPHOS]Rh(COD)$^+$BF$_4^-$. This represents an unexpected switch in absolute stereochemistry when compared to hydrogenation of the ester substrate 1a (Scheme 3). In addition, the enantioselectivity achieved in the hydrogenation of the salt 4a is much higher, typically at least about 95% e.e. The choice of cation Y does not appear to be critical, since comparable enantioselectivities are observed with metallic cations (e.g., K$^+$) and non-metallic cations (e.g., tert-butyl ammonium). Without being bound by theory, the contrasting properties of substrates 1a and 4a may derive from binding interactions between functional groups of each substrate and the rhodium center in the catalyst, which in turn may influence both the direction and degree of facial selectivity during hydrogenation of the olefin. Thus, in the hydrogenation of the ester 1a, the cyano substituent may participate in binding to the catalyst. This effect appears to be entirely overridden in hydrogenation of the salt 4a, in which binding by the carboxylate group is likely to be dominant.

Scheme 4

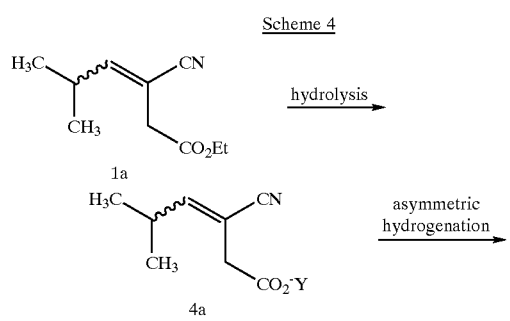

-continued

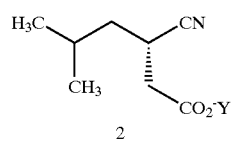

As a further embodiment, the invention provides novel compounds of the formula 4

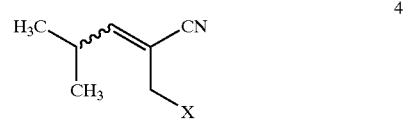

wherein X is CO$_2$H or CO$_2$—Y, and where Y is a cation as described above in Scheme 1. These compounds are useful substrates in the synthesis of pregabalin.

In another preferred embodiment of the invention, the final pregabalin product may be selectively recrystallized with (S)-mandelic acid to provide still further enhanced enrichment of the desired S-isomer. Thus, high levels of the (R)-enantiomer (up to at least 50%) can be removed by classical resolution via the S-mandelic acid salt (U.S. Pat. No. 5,840,956; U.S. Pat. No. 5,637,767). Suitable solvents for such selective recrystallizations include, for example, water or an alcohol (e.g., methanol, ethanol, and isopropanol, and the like) or a mixture of water and an alcohol. In general, excess mandelic acid is used. It is also noted that mandelic acid can be used in combination with another acid.

Alternatively, pregabalin containing low levels (≦1%) of the (R)-enantiomer, can be enriched to >99.9% of the (S)-enantiomer by simple recrystallization from, for example, water/isopropyl alcohol. Pregabalin containing higher levels (up to 3.5%) of the (R)-enantiomer), can also be enriched by simple recrystallization from, for example, water/isopropyl alcohol, although successive recrystallizations are usually required to reach >99.9% of the (S)-enantiomer. "Substantially pure" pregabalin, as used herein, means at least about 95% (by weight) S-enantiomer, and no more than about 5% R-enantiomer.

The following detailed examples further illustrate particular embodiments of the invention. These examples are not intended to limit the scope of the invention and should not be so construed. The starting materials and various intermediates may be obtained from commercial sources, prepared from commercially available compounds, or prepared using well-known synthetic methods well-known to those skilled in the art of organic chemistry.

Preparations of Starting Materials
3-Hydroxy-4-methyl-2-methylene pentanenitrile

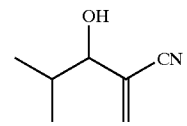

A 250 mL, three-necked, round-bottom flask with overhead stirring is charged with 0.36 g (1.6 mmol) of 2,6-di-tert-butyl-4-methylphenol, 37 g (0.33 mol) of 1,4-diazabicyclo[2,2,2]octane, 60 mL (0.66 mol) of isobutyraldehyde, 52 mL (0.79 mol) of acrylonitrile, and 7.2 mL (0.4 mol) of water. The reaction mixture is stirred at 50°

C. for 24 hours, cooled to 25° C., and quenched into a solution of 33 mL (0.38 mol) of hydrochloric acid and 100 mL of water. The product is extracted with 120 mL of methylene chloride. The aqueous acid layer is extracted again with 25 mL of methylene chloride. The combined methylene chloride layers are concentrated by rotary evaporation to provide 79.9 g (96.7%) of 3-hydroxy-4-methyl-2-methylenepentanenitrile as a yellow oil (which may solidify to a white solid on standing), 96.7% (area under the curve) by HPLC assay, which may be used in the next step without further purification.

Carbonic acid 2-cyano-1-isopropyl-allyl ester ethyl ester

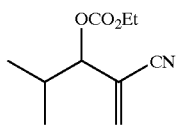

A nitrogen-purged 5 L, three-necked, round-bottom flask with overhead stirring is charged with 150 g (1.2 mol) of 3-hydroxy-4-methyl-2-methylenepentanenitrile, 1.0 L of methylene chloride, and 170 mL (2.1 mol) of pyridine. The solution is cooled at 10° C. to 15° C. in an ice bath. Using a 1 L graduated addition funnel, a mixture of 0.5 L of methylene chloride and 200 mL (2.1 mol) of ethyl chloroformate is added slowly while maintaining the reaction temperature at 20° C.±5° C. The reaction is stirred at 22° C.±3° C. for about two additional hours. The reaction solution is poured into a 6 L separatory funnel containing 200 mL (2.3 mol) of hydrochloric acid and 1.25 L of water. The lower organic layer is washed again with a solution of 60 mL (0.7 mol) of HCl and 0.5 L of water. The organic layer is dried over anhydrous magnesium sulfate (30 g), filtered, and concentrated by rotary evaporation to provide 226 g of carbonic acid 2-cyano-1-isopropyl-allyl ester ethyl ester as a yellow oil which may be used in the next step without further purification.

Acetic acid 2-cyano-1-isopropyl-allyl ester (using acetyl chloride)

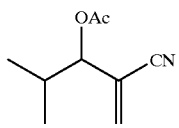

A nitrogen-purged 5 L, three-necked, round-bottom flask with overhead stirring is charged with 50 g (0.4 mol) of 3-hydroxy-4-methyl-2-methylenepentanenitrile, 0.4 L of methylene chloride, and 80 mL (1 mol) of pyridine. The solution is cooled at 10° C. to 15° C. in an ice bath. Using a 500 mL graduated addition funnel, a mixture of 100 mL of methylene chloride and 43 mL (0.6 mol) of acetyl chloride is added slowly while maintaining the reaction temperature at 25° C.±5° C. The reaction is stirred at 22° C.±3° C. for about one additional hour. The reaction solution is poured into a 4 L separators funnel containing 85 mL (1.0 mol) of hydrochloric acid and 750 mL of water. The lower organic layer is washed again with a solution of 20 mL (0.2 mol) of HCl and 250 mL of water. The organic layer is dried over anhydrous magnesium sulfate (20 g), filtered, and concentrated by rotary evaporation to provide 66 g of acetic acid 2-cyano-1-isopropyl-allyl ester as a yellow oil which may be used in the next step without further purification.

Acetic acid 2-cyano-1-isopropyl-allyl ester (using acetic anhydride)

To a 500 mL, four-necked, round-bottom flask equipped with an overhead stirrer, a temperature probe, a reflux condenser, and a nitrogen inlet is charged acetic anhydride (40 mL, 0.45 mol). This solution is heated to 50° C. and a solution of 3-hydroxy-4-methyl-2-methylenepentanenitrile (50 g, 0.40 mol) and 4-(dimethylamino)pyridine (1.5 g) in tetrahydrofuran (25 mL) is added over 35 minutes. A temperature of 50° C. to 63° C. is maintained without external heating. After the addition is complete, the reaction mixture is heated at 60° C. for 75 minutes. The solution is cooled to 30° C. and the cooled reaction mixture is diluted with 30 mL of tert-butylmethyl ether (MTBE) and 25 mL of water. This mixture is cooled to 10° C. and a solution of 50% aqueous sodium hydroxide (37 g, 0.46 mol) diluted with 45 mL of water is added with cooling, such that the temperature is maintained at about 15° C. For the final pH adjustment, 50% aqueous sodium hydroxide 9.8 g (0.12 mol) is added dropwise to a final pH of 9.4. After adding 10 mL of water and 10 to 15 mL of MTBE, the reaction mixture is phased and separated. The upper organic product layer is separated and washed with 25 mL of brine, dried over magnesium sulfate, and concentrated in vacuo to provide 63.7 g (95%) of acetic acid 2-cyano-1-isopropyl-allyl ester as a pale yellow oil.

Ethyl 3-cyano-5-methyl hex-3-enoate

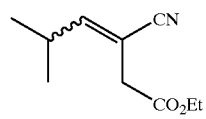

A high pressure reactor with overhead stirring is charged with 3.0 g (13.4 mmol) of palladium acetate, 7.0 g (26.8 mmol) of triphenylphosphine, and 226 g (0.92 mol) of the crude oil containing carbonic acid 2-cyano-1-isopropyl-allyl ester ethyl ester, and 500 mL of ethanol. Carbon monoxide is introduced at 280 to 300 psi, and the mixture is heated at 50° C. overnight with stirring. The red-brown solution is filtered through celite to remove solids. The filtrate is concentrated by rotary evaporation to provide 165 g of crude yellow oily product, ethyl-3-cyano-5-methyl hex-3-enoate, which assays 84% (area) by gas chromatography (GC) as a mixture of the E and Z geometric isomers. The crude product may be used without further purification, or alternatively, is purified by vacuum distillation (0.6–1.0 mm Hg at 60° C.–70° C.) to give a colorless oil which assays ≧95% (area) by GC.

Ethyl 3-cyano-5-methyl hex-3-enoate (using, KBr)

A high pressure reactor with overhead stirring is charged with palladium acetate (0.52 g, 2.3 mmol), triphenylphosphine (0.65 g, 2.3 mmol), potassium bromide (5.5 g, 4.8 mmol), a crude oil containing carbonic acid 2-cyano-1-isopropyl-allyl ester ethyl ester (240 g, 1.2 mole), triethylamine (2.2 g, 22 mmol), ethanol 2B (45 mL), and acetonitrile (200 mL). Carbon monoxide is introduced at 50 psi. and the mixture is heated at 50° C. overnight with stirring. The pressure of the reactor is released to 10 to 15 psi after about 1, 3, and 6 hours and is refilled with carbon monoxide to 50 psi. The reaction mixture is filtered through celite to remove solids. The filtrate is concentrated in vacuo and 800 mL of hexane is added. The resulting mixture is washed twice with 500 mL of water, and the hexane is removed in vacuo to provide 147 g of crude ethyl 3-cyano-5-methyl hex-3-enoate as an oil. This crude product is purified by fractional distillation (0.7 mm Hg at 60° C.–70° C.).

Ethyl 3-cyano-5-methyl hex-3-enoate (using NaBr)

A high pressure reactor with overhead stirring is charged with 0.5 g (0.5 mmol) of tris(dibenzylideneacetone)dipalladium (0), 0.5 g (2.0 mmol) of triphenylphosphine, 0.5 g (5.0 mmol) of sodium bromide, 4.5 mL (25.0 mmol) of diisopropylethylamine, 8.35 g (50.0 mmol) of acetic acid 2-cyano-1-isopropyl-allyl ester, and 100 mL of ethanol. Carbon monoxide is introduced at 40 to 50 psi, and the mixture is heated at 50° C. for 24 hours with stirring. The brown solution is filtered through celite to remove solids. The filtrate is concentrated by rotary evaporation. The concentrated reaction mixture is diluted with 150 mL of methyl tert-butyl ether and washed with water. The solvent is removed on a rotary evaporator to provide 7.7 g of crude yellow oily product, ethyl-3-cyano-5-methyl hex-3-enoate (85 area percent on GC assay). The crude product may be used without further purification or alternatively, may be purified by vacuum distillation (0.6–1.0 mm Hg at 60° C.–70° C.).

EXAMPLE 1
Synthesis of 3-cyano-5-methylhex-3-enoic acid salts

A. tert-Butylammonium salt of 3-cyano-5-methylhex-3-enoic acid

| Material | MWt | Quantity | mmol |
|---|---|---|---|
| Ethyl 3-cyano-5-methylhex-3-enoate | 181.24 | 20.02 g | 110 |
| LiOH H$_2$O | 41.96 | 13.0 g | 310 |
| Tetrahydrofuran | | 75 mL | |
| Water | | 25 mL | |
| Hydrochloric Acid (2N) | | As required | |
| Ethyl Acetate | | As required | |
| tert-butylamine | 73.14 | 9.27 g | 127 |

Ethyl 3-cyano-5-methylhex-3-enoate (mixture of E and Z isomers) and lithium hydroxide hydrate are suspended in a mixture of tetrahydrofuran and water. The slurry is vigorously stirred for 4 hours at room temperature. The mixture is acidified to pH 2 (3N HCl) and extracted into ethyl acetate (3×150 mL). The combined organic layers are dried (MgSO$_4$), and the solvent is removed in vacuo to give crude 3-cyano-5-methylhex-3-enoic acid. The crude acid is dissolved in ethyl acetate (400 mL), and a solution of tert-butylamine in ethyl acetate (20 mL) is added. The temperature of the solution rises approximately 10° C. as a mass of white crystalline solid precipitates. The product is collected by filtration and dried in vacuo. Yield 22.15 g, 97.9 mmol, 89%.

A1. tert-Butyl ammonium 3-cyano-5-methylhex-3-enoate (alternative method)

To an appropriately sized 3-necked round-bottomed flask is charged 50 g of an oil containing ethyl 3-cyano-5-methylhex-3-enoate (29.9 g contained weight, 165 mmol). A solution of KOH (91%, 10.2 g, 165.1 mmol) in 50 mL of water is charged to the ester solution over 20 minutes, and the solution is allowed to stir for 1 additional hour. Water (50 mL) is charged, and the solution is concentrated to 80 mL in vacuo. The water solution is washed with MTBE (100 mL), and the product-containing aqueous layer is acidified to a pH of 1 with concentrated hydrochloric acid (20 mL). The resulting acid is extracted into MTBE (100 mL). The product-containing MTBE solution is concentrated in vacuo. The resultant oil is dissolved in isopropyl alcohol (58 mL) and heptane (85 mL), and this solution is filtered through celite. The filter cake is washed with a mixture of isopropyl alcohol (58 mL) and heptane (85 mL). tert-Butylamine is charged to the solution to form a thick gel-like slurry. The slurry is heated to reflux to give a solution. The solution is allowed to slowly cool to room temperature. The resultant slurry is cooled to 0° C. to 5° C. for 1.5 hours then filtered and washed with a mixture of isopropyl alcohol (50 mL) and heptane (150 mL). The solid is dried under vacuum at 45° C. to 50° C. to give 23.1 g (62%) of tert-butyl ammonium 3-cyano-5-methylhex-3-enoate as a white solid which is a mixture of E and Z isomers. The Z isomer can be obtained in greater than 99% isomeric purity by recrystallization from isopropyl alcohol and heptane.

B. Potassium salt of 3-cyano-5-methylhex-3-enoic acid

| Material | Source | MWt | Quantity | mmol |
|---|---|---|---|---|
| Ethyl 3-cyano-5-methylhex-3-enoate | PD 61966X130 | 181.24 | 90.8 g | 501 |
| Potassium hydroxide 85% | Aldrich | 56.11 | 33.1 g | 501 |
| Methanol | Fisher | | 90 mL | |
| tert-Butylmethyl ether | Fisher | | 900 mL | |

Potassium hydroxide is dissolved in methanol (70 mL) and added to rapidly stirring ethyl 3-cyano-5-methylhex-3-enoate (mixture of E and Z geometric isomers) at such a rate as to maintain the temperature below 45° C. The residual methanolic potassium hydroxide is rinsed into the mixture with extra methanol (2×10 mL). The mixture is heated at 45° C. for 1 hour and then allowed to cool to room temperature during which time a crystalline solid forms, tert-Butylmethyl ether (600 mL) is slowly added to the mixture with vigorous stirring. The solid is collected on a course frit filter, washed with tert-butylmethyl ether (3×100 mL), and dried to provide the title compound. Yield 83.9 g, 439 mmol, 88%.

EXAMPLE 2
Asymmetric Hydrogenation of 3-cyano-5-methylhex-3-enoic acid salts

A. tert-Butylammonium salt of (S)-3-cyano-5-methylhexanoic acid

| Material | MWt | Quantity | mmol |
|---|---|---|---|
| tert-Butylammonium salt of 3-cyano-5-methylhex-3-enoic acid | 226.33 | 19.0 g | 84 |
| [(R,R)-MeDuPHOS]Rh(COD) BF$_4^-$ | 604 | 49.6 mg | 0.082 |
| Methanol | 32 | 200 mL | |
| Hydrogen | 2 | 44 psi (3 bar) | |

A round-bottom flask is charged with the tert-butylammonium salt of 3-cyano-5-methylhex-3-enoic acid (from Example 1A) and [(R,R)-MeDuPHOS]Rh(COD)⁺ BF₄⁻ under a nitrogen atmosphere. Deoxygenated methanol is added via syringe, and the solution is deoxygenated by repeated partial evacuation and back filling with nitrogen. A 600 mL PARR pressure vessel is purged with hydrogen by pressurizing and releasing the pressure three times. The vessel is then heated to 55° C. The solution of substrate and catalyst is transferred to the reactor by cannula, and the vessel is again purged with hydrogen before finally pressurizing to 3 bar (44 psi). Stirring is started and hydrogen up-take commenced. The vessel is repeatedly recharged to 3 bar pressure until hydrogen uptake ceases (~45 min). After stirring under pressure at 55° C. for an additional 1 hour, heating is discontinued. Once the reactor cools to room temperature, the hydrogen pressure is released, the vessel is purged with nitrogen, and the reaction mixture is transferred to a round-bottom flask. The solvent is removed in vacuo to give the crude product. A small sample is removed and converted to (S)-3-cyano-5-methylhexanoic acid by treatment with aqueous hydrochloric acid and extraction into dichloromethane, GC analysis shows 100% conversion to the reduced cyano alkane with 95.0% e.e. (S).

B. Potassium salt of (S)-3-cyano-5-methylhexanoic acid (substrate to catalyst (S/C) ratio 1000/1)

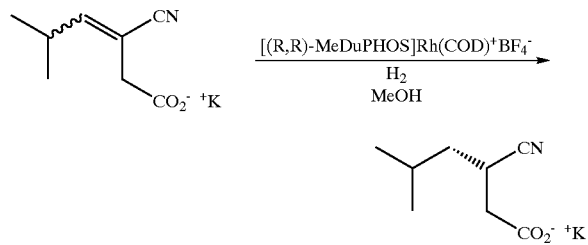

| Material | MWt | Quantity | mmol |
|---|---|---|---|
| Potassium salt of 3-evano-5-methylhex-3-enoic acid | 191.3 | 11.03 g | 57.7 |
| [(R,R)-MeDuPHOS]Rh(COD)BF₄⁻ | 604 | 11 mg in 10 mL MeOH | 18.2 × 10⁻³ S/C = 1000 ʷ/w |
| Methanol | 32 | 100 mL | |
| Hydrogen | 2 | 60 psi (4 bar) | |

A glass liner is charged with the potassium salt of 3-cyano-5-methylhex-3-enoic acid (from Example 1B) and methanol and placed in a 600 mL PARR hydrogenation vessel. The vessel is purged with nitrogen and then with hydrogen via charging to 60 psi and stirring for 10 minutes to ensure thorough equilibration of gases and releasing of the pressure on five cycles. The vessel is heated to 45° C., and a solution of [(R,R)-MeDuPHOS]Rh(COD)BF₄⁻ in deoxygenated methanol (11 mg in 10 mL) is added via syringe. The vessel is again purged with hydrogen and then pressurized to 60 psi with stirring. Periodically, hydrogen is added to maintain the pressure between 50 to 65 psi. Hydrogen uptake ceases after 120 minutes. After 2 hours, the mixture is cooled to room temperature, the pressure is released, and the solvent is removed to give the crude product. A small sample is removed and acidified with 1 N HCl to give (S)-3-cyano-5-methylhexanoic acid. GC analysis shows >99% conversion with 96.7% e.e S isomer.

C. Potassium salt of (S)-3-cyano-5-methylhexanoic acid (substrate to catalyst (S/C) ratio 3200/1,640 mmol)

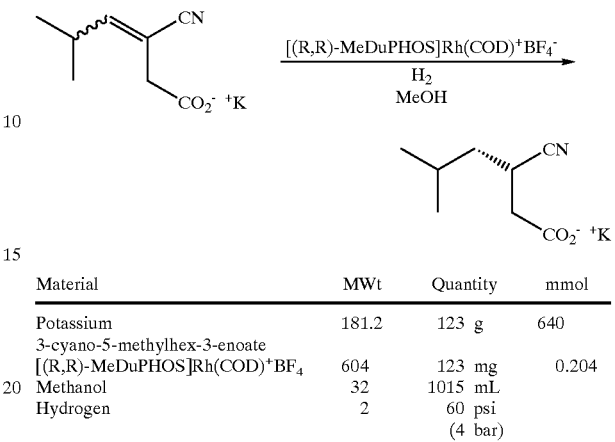

| Material | MWt | Quantity | mmol |
|---|---|---|---|
| Potassium 3-cyano-5-methylhex-3-enoate | 181.2 | 123 g | 640 |
| [(R,R)-MeDuPHOS]Rh(COD)⁺BF₄ | 604 | 123 mg | 0.204 |
| Methanol | 32 | 1015 mL | |
| Hydrogen | 2 | 60 psi (4 bar) | |

A glass liner was charged with potassium 3-cyano-5-methylhex-3-enoate (from Example 1B) and methanol (1000 mL). The liner was placed in a 2 L PARR hydrogenation vessel. The vessel was purged with nitrogen and then with hydrogen via charging to 60 psi and releasing the pressure over five cycles. The vessel was then heated to 45° C. A solution of [(R,R)-MeDuPHOS]Rh(COD)⁺BF₄⁻ in deoxygenated methanol (15 mL) was added via syringe. The vessel was again purged with hydrogen three times then pressurized to 65 psi and stirring commenced. Periodically, hydrogen was added to maintain the pressure between 50 to 65 psi. Hydrogen uptake ceased after 2½ hours, the vessel was cooled to room temperature and left to stir overnight. The pressure was released, the mixture was transferred to a flask, and the solvent was removed in vacuo to give the product. A small sample was removed and converted to methyl (S)-3-cyano-5-methylhex-3-enoate. Gas chromatographic analysis showed >99% conversion 97.5% e.e.

D. tert-Butylammonium salt of (S)-3-cyano-5-methylhexanoic acid (S/C ratio 2700/1,557 mmol)

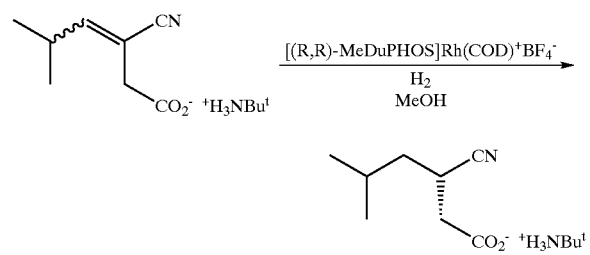

| Material | MWt | Quantity | mmol |
|---|---|---|---|
| tert-Butylammonium 3-cyano-5-methylhex-3-enoate | 226.33 | 125.8 g | 557 |
| [(R,R)-MeDuPHOS]Rh(COD)⁺BF₄⁻ | 604 | 125 mg | 0.082 |
| Methanol | 32 | 200 mL | |
| Hydrogen | 2 | 50–65 psi | |

A glass liner was charged with tert-butylammonium 3-cyano-5-methylhex-3-enoate and methanol (1000 mL). The liner was placed in a 2 L PARR hydrogenation vessel. The vessel was purged with nitrogen and then with hydrogen via charging to 60 psi and releasing the pressure over five cycles. The vessel was then heated to 45° C. A solution of [(R,R)-MeDuPHOS]Rh(COD)$^+$BF$_4^-$ in deoxygenated methanol (15 mL) was added via syringe. The vessel was again purged with hydrogen three times then pressurized to 65 psi and stirring commenced. Periodically, hydrogen was added to maintain the pressure between 50 to 65 psi. Hydrogen uptake ceased after 4 hours, then after a further 1 hour, the vessel was cooled to room temperature. The pressure was released, the mixture was transferred to a flask, and the solvent was removed in vacuo to give the product. A small sample was removed and converted to methyl (S)-3-cyano-5-methylhex-3-enoate by reaction with methanol and 1N HCl. GC analysis showed >99% conversion 97.7% e.e.

E. Potassium salt of 3-cyano-5-methylhexanoic acid generated in situ from ethyl 3-cyano-S-methylhex-3-enoate

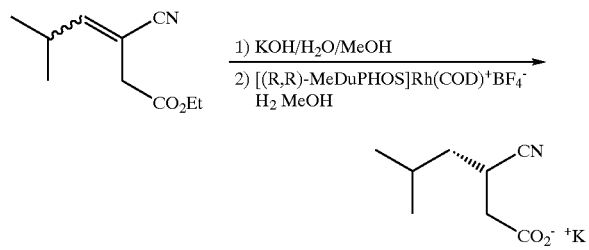

| Material | MWt | Quantity | mmol |
|---|---|---|---|
| Ethyl 3-cyano-5-methylhex-3-enoate | 181.2 | 10.81 g | 59.7 |
| Potassium hydroxide | | 11.68 mL | 58.4 |
| [(R,R)-MeDuPHOS]Rh(COD) BF$_4^-$ | 604 | 18.0 mg | 29.8 × 10$^{-3}$ |
| Methanol | 32 | 120 mL | |
| Water | 18 | 18 mL | |
| Hydrogen | 2 | 60 psi (4 bar) | |

A glass liner is charged with ethyl 3-cyano-5-methylhex-3-enoate (starting material prepared above), methanol (100 mL), and water (18 mL). Potassium hydroxide is added with stirring. A liner is placed in a 600 mL PARR hydrogenation vessel. The vessel is purged with nitrogen and then with hydrogen via charging to 60 psi and releasing the pressure on 5 cycles. The vessel is heated to 55° C. A solution of [(R,R)-MeDuPHOS]Rh(COD)$^+$BF$_4^-$ in deoxygenated methanol (18.0 mg in 20 mL) is added via syringe. The vessel is again purged with hydrogen and then pressurized to 60 psi with stirring. Periodically, hydrogen is added to maintain the pressure between 50 to 60 psi. Hydrogen uptake ceases after 5 hours. After an additional 1 hour, the mixture is cooled to room temperature, and the pressure is released. The mixture is transferred to a flask, and the solvent is removed in vacuo to give the product. A small sample is removed and converted to (S)-3-cyano-5-methylhexanoic acid by reaction with 1N hydrochloric acid. GC analysis shows 98.7% conversion to the desired cyano alkanoic salt with 96.6% e.e S isomer.

EXAMPLE 3

Hydrogenation of ethyl 3-cyano-5-methylhex-3-enoate

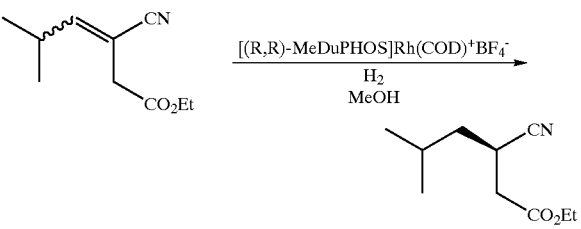

| Material | MWt | Quantity | mmol |
|---|---|---|---|
| Ethyl 3-cyano-5-methylhex-3-enoate | 181 | 0.36 g | 2.00 |
| [(R,R)-Me-DuPHOS]Rh(COD) BF$_4^-$ | 604 | 1.2 mg | 2 × 10$^{-3}$ |
| Methanol | | 5 mL | |
| Hydrogen | | 60 psi (4 bar) | |

A. The reaction is carried out in a 50 mL micro reactor fitted with an injection septum and valve. A micro reactor is used in conjunction with a glass liner. Methanol is deoxygenated by four cycles of partial evacuation and refilling with nitrogen while stirring. A liner charged with ethyl 3-cyano-5-methylhex-3-enoate and a magnetic stir bar is placed in the micro reactor, and the micro reactor is subsequently assembled. A hydrogen atmosphere is established by three cycles of charging the vessel with hydrogen and releasing the pressure. Methanol (4 mL) is added, and the vessel is then placed in an oil bath on a stirrer hotplate at 60° C. and allowed to come to thermal equilibrium (internal temp ~45° C.). A small Schlenk tube is charged with [(RR)-Me-DuPHOS]Rh(COD)$^+$BF$_4^-$ and a nitrogen atmosphere established by four cycles of partial evacuation and refilling with nitrogen. The catalyst is dissolved in methanol such as to give a solution containing 1.2 mg of catalyst in 1 mL of solvent. One milliliter of the catalyst solution is added via syringe to the micro reactor. The vessel is again purged by pressurizing with hydrogen to 60 psi and releasing the pressure for a further four cycles. The vessel is then charged to 60 psi and is stirred until hydrogen uptake is judged to have ceased (~3 hours). The reactor is removed from the oil bath and allowed to cool. The pressure is then released and the solvent removed in vacuo. GC analysis shows 99% conversion, 22.7% e.e. (R).

B. By following the general procedure of Example 3.1, 200 mg (1.190 mmol) of methyl 3-cyano-5-methyl-hex-3-enoate was dissolved in 3 mL of methanol and reacted with hydrogen gas (60 psi) in the presence of 43 mg (0.06 mmol) of [(R,R)-Et-DuPHOS]Rh(COD)$^+$BF$_4^-$ to afford 10% conversion to methyl 3-cyano-5-methylhexanoate having 33% e.e. (R).

EXAMPLE 4

Synthesis of Pregabalin

A. Conversion of potassium salt of (S)-3-cyano-5-methylhexanoic acid to pregabalin The S-cyano acid, potassium salt (prepared as described in Example 2B, 94.9% S-isomer, 8.0 g, 41.4 mmol) is charged along with potassium hydroxide (91% flake, 44.0 mg gross, 40.0 mg net, 0.7 mmol), water (15 mL), and 2B EtOH (i.e., denatured with toluene) (10 mL) to a PARR bottle containing sponge nickel catalyst (A-7000, Activated Metals and Chemicals. Inc., P.O. Box 4130, Severville, Tenn. 37864, 5 g, water wet). The slurry is shaken on a PARR shaker under 50 psi hydrogen at room temperature overnight.

The slurry is filtered through a pad of Supercel. The filter cake is rinsed with water (20 mL) and 2B EtOH (7 mL). The combined filtrate is mixed with glacial acetic acid (2.4 mL, 2.5 g, 41.6 mmol) and heated at 70° C. for 30 minutes. The mixture is cooled to 0° C. and the solid is collected by filtration, washed with isopropanol (50 mL), and dried to give 3.2 g of product (20 mmol, 49% yield). HPLC assay of the material shows 99.7% (area under the curve) 3-isobutyl GABA. Enantiomer analysis (HPLC) indicates the 3-isobutyl GABA as a mixture of isomers: 97.82% is the desired S-isomer (pregabalin), and 2.18% is the undesired R-isomer.

B. Conversion of tert-butyl ammonium salt of (S)-3-cyano-5-methylhexanoic acid to pregabalin The S-cyano acid, tert-butyl ammonium salt (prepared or described in Example 2A, 97% S-isomer, 8.0 g, 35.0 mmol) is charged along with potassium hydroxide (91% flake, 2.2 g gross, 2.0 g net, 35.6 mmol), water (15 mL), and 2B EtOH (11 mL) to a PARR bottle containing sponge nickel catalyst (A-7000, 5 g, water wet). The slurry is shaken on a PARR shaker under 50 psi hydrogen at room temperature overnight.

The slurry is filtered through a pad of Supercel. The filter cake is rinsed with water (20 mL) and 2B EtOH (ethanol denatured with toluene) (7 mL). The combined filtrate is charged with glacial acetic acid (4.1 mL, 4.3 g, 71.6 mmol). The resulting solution is heated to 70° C. and then allowed to cool slowly to room temperature. The reaction slurry is then stirred at 0° C. to 5° C. for 6 hours and filtered. The solid is rinsed with IPA (50 mL) and is dried for 2 days in a vacuum oven to give a solid weighing 3.4 g (61.0% overall yield). HPLC analysis identifies the product as 97.20% (area) 3-isobutyl GABA, 99.92% of which is the desired S-isomer (pregabalin).

An argon-purged 600 mL pressure reactor is charged tert-butyl ammonium 3-cyano-5-methylhex-3-enoate (prepared as described in Example 1A 36 g, 159.1 mmol) and [(R,R)MeDUPHOS]Rh(COD)BF$_4$ (0.054 g, 0.0894 mmol). The reactor is pressure purged with argon (3×50 psi). To a 1000 mL reactor is charged 360 mL of methanol. The methanol is pressure purged with argon (3×50 psi). The methanol is then charged to the reactor containing the substrate and catalyst. The solution is pressure purged with argon (3×50 psi), and then the reactor is pressurized to 50 psi with hydrogen and stirred overnight at 27° C. to 33° C. The hydrogen pressure is released, and the solution purged with argon. The solution is transferred into a vessel containing a solution of potassium hydroxide (91%, 10.3 g, 167 mmol) in 90 mL of water. The solution is concentrated to about 180 mL in vacuo. The concentrated solution is transferred to a 600 mL pressure reactor containing sponge nickel A-7000 (12.0 g, 50% water wet). The solution is purged with argon (3×50 psi), and then the reactor is pressured to 50 psi with hydrogen and stirred overnight. The hydrogen pressure is released. The solution is purged with argon and filtered. The filter cake is washed with 90 mL of methanol. The filtrate is concentrated in vacuo to remove the methanol, and 72 mL of isopropyl alcohol is charged. The solution is heated to 65° C. Glacial acetic acid (9.4 mL, 171 mmol) is charged, and the solution is heated to 73° C. The solution is quickly cooled to 50° C., then slowly cooled to room temperature. The slurry is cooled to 0° C. to 5° C. for 3.5 hours. The slurry is filtered, and the cake is washed with isopropyl alcohol. The solid is dried under vacuum at 45° C. to give 18.4 g (73%) of pregabalin as a white solid (99.89% S).

An argon-purged 170 L reactor is charged with tert-butyl ammonium 3-cyano-5-methylhex-3-enoate (10 kg, 44.2 mol prepared as described in Example 1A) and [(R,R) MeDUPHOS]Rh(COD)BF$_4$ (0.015 kg, 0.0025 mol). The reactor is pressure purged with argon (3×50 psi). To a 170 L still is charged 100 L of methanol. The reactor is evacuated under vacuum, and then the vacuum is broken with argon. The still is pressurized to 50 psi with argon and then vented. This entire purge procedure is repeated twice more. The methanol is charged to the reactor containing the substrate and catalyst. The solution is pressure purged with argon (3×50 psi), and then the vessel is pressurized to 50 psi with hydrogen and stirred overnight at 27° C. to 33° C. The hydrogen pressure is released, and the solution is purged with nitrogen. The solution is filtered into a 170 L still containing a solution of potassium hydroxide (91%, 2.9 kg, 46.4 mol) in 25 L of water. A 5 L wash of methanol is used to clean the transfer line. The filtrate is concentrated to a volume of 50 to 60 L by vacuum distillation. This concentrated solution is transferred to a 170 L reactor containing sponge nickel A-7000 (5.0 kg, 50% water wet). The solution is purged with nitrogen (3×50 psi). Then, the reactor is pressurized to 50 psi with hydrogen and stirred overnight. The hydrogen pressure is released, and the solution is purged with nitrogen. The solution is filtered into a 170 L still, and the filter and lines are rinsed with 30 L of methanol. The filtrate is concentrate by vacuum distillation to a volume of 25 to 35 L, and then 30 L of isopropyl alcohol is charged. The solution is concentrated by vacuum distillation to about 18 L. Isopropyl alcohol (20 L) and water (5 L) are charged, and the solution is heated to 60° C. to 65° C. Glacial acetic acid (2.9 kg, 47.7 mol) is charged, and the solution is heated to reflux. Water (8 L) is charged to make a solution. The solution is quickly cooled to 50° C. and then cooled to −5° C.±5° C. over about 5.5 hours. The slurry is held at −5° C.±5° C. for about 10 hours and then filtered and washed with isopropyl alcohol (10 L). The solvent-wet filter cake is charged to a 170 L still followed by water (20 L) and isopropyl alcohol (40 L). The slurry is heated to reflux to make a clear solution, which is filtered into a 170 L reactor. The solution is quickly cooled to 50° C. and then cooled to −5° C.±5° C. over about 3.5 hours. The slurry is held a −5° C.±5° C. for about 16 hours. The solid is filtered and washed with isopropyl alcohol (10 L). The solid is dried under vacuum at 45° C. for 3 days to give 4.0 kg (57%) of pregabalin as a white solid (99.84% S).

EXAMPLE 5

Hydrogenation of 3-cyano-5-methylhex-3-enoic acid (free acid)

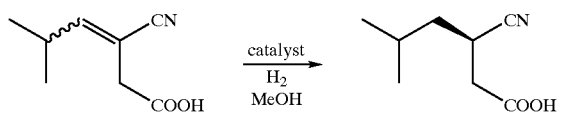

| Material | MWt | Quantity | mmol |
|---|---|---|---|
| 3-Cyano-5-methylhex-3-enoic acid | 153 | 200 mg | 1.307 |
| [(S,S)-Me-BPE]Rh(COD)$^+$BF$_4^-$ | 618.48 | 20 mg | 0.0327 (2.5 mol %) |
| Methanol | | 4 mL | |
| Hydrogen | | 50 psi (4 bar) | |

A. The free hexanoic acid was dissolved in methanol, and the chiral catalyst was added to the solution. The mixture was shaken at 24° C. for 19 hours under hydrogen at 50 psi. A sample was analyzed by proton NMR, and the reaction was determined to be 24% complete, with the cyano hexanoic acid having 95% e.e. (S).

One equivalent amount (0.18 mL) of triethylamine was added to the reaction mixture, and shaking was continued for 5 additional hours (24° C. 50 psi). The reaction mixture was filtered, and the solvent was removed by evaporation. The product was analyzed by proton NMR and shown to contain about 43% of the desired (S)-3-cyano-5-methylhexanoic acid having 95% e.e. for the S-enantiomer.

B. The above procedure was followed to react 250 mg (1.634 mmol) of 3-cyano-5-methylhex-3-enoic acid with hydrogen (50 psi) in the presence of 8 mg (0.01634 mmol) of [(S,S)-Et-BPE]Rh(COD)$^+$BF$_4^-$ and 0.023 mL (0.1634 mmol; 0.1 eq) of triethylamine in 5 mL of methanol at 24° C. for 40 hours. The reaction mixture was filtered, the solvent was removed by evaporation, and the product was shown by proton NMR to be 71% (S)-3-cyano-5-methylhexanoic acid with 84% e.e. for the S-enantiomer.

C. The above procedure was repeated, except that no base was added to the reaction mixture. The product was shown by proton NMR to be 26%, (S)-3-cyano-5-methylhexanoic acid having 91% e.e. for the S-enantiomer.

D. The above procedure was followed to react 200 mg (1.307 mmol) of 3-cyano-5-methylhex-3-enoic acid with hydrogen (50 psi, 100 hours) in the presence of 10 mg (0.01307 mmol) of [(S,S)-Et-DuPHOS]Rh(COD)$^+$BF$_4^-$. The product was shown by proton NMR to be 82% (S)-3-cyano-5-methylhexanoic acid having 56% e.e. for the S-enantiomer.

E. The procedure of Example 5D was repeated, except that 0.1 eq. (0.02 mL, 0.1307 mmol) of triethylamine was added to the reactive mixture. The reaction was stopped after 16 hours, and the product was shown to be 86% (S)-3-cyano-5-methylhexanoic acid with 68% e.e. for the S-enantiomer.

F. The procedure of Example 5E was repeated, except that 1 eq. (0.18 mL, 1.307 mmol) of triethylamine was added to the reaction mixture, and the reaction was stopped at 16 hours. The product was shown by proton NMR to be 92% converted to (S)-3-cyano-5-methylhexanoic acid having 56% e.e. for the S-enantiomer.

G. By following the general procedures from above, 250 mg (1.634 mmol) of 3-cyano-5-methylhex-3-enoic acid was reacted with hydrogen (50 psi, 16 hours. 24° C.) in the presence of 12 mg (0.01634 mmol) of [(R,R)-DIPAMP]Rh(COD)$^+$BF$_4^-$ in methanol (10 mL) to provide 51% of 3-cyano-5-methylhexanoic acid having 72% e.e. for the R-enantiomer.

EXAMPLE 6

Recrystallization of Pregabalin

Pregabalin solid (117 kg, 735 mol) containing 0.6% of the (R)-enantiomer is combined with water (550 L; 4.7 L/kg pregabalin) and isopropyl alcohol (1100 L: 9.4 L/kg pregabalin). The mixture is heated to dissolve the solids (about 75° C.±5° C.), filtered while hot, and cooled to 0° C.±5° C. to crystallize the product. The solid is collected on a centrifuge and rinsed with isopropyl alcohol. The damp solid is dried under vacuum at 35° C. to 45° C. and then milled to give 91.8 kg (78.5%) of pregabalin as a white crystalline solid. The enantiomer ratio is 99.94% (S)-enantiomer pregabalin) and 0.06% of the (R)-enantiomer.

The invention and the manner and process of making and using it, are now described in such full, clear, concise, and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as the invention, the following claims conclude this specification.

What is claimed is:

1. A method for preparing an (S)-3-cyano-5-methylhexanoic acid derivative of the formula

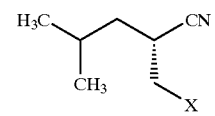

wherein X is CO$_2$H or CO$_2$—Y, and where Y is a cation;
the method comprising asymmetric catalytic hydrogenation of an alkene of the formula

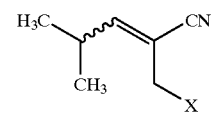

in the presence of a chiral catalyst and solvent, wherein the chiral catalyst comprises a chiral phosphine ligand.

2. A method according to claim 1, wherein X is CO$_2$—Y.

3. A method according to claim 1, wherein the chiral catalyst is a rhodium complex of an (R,R)-DuPHOS ligand, the ligand having the formula

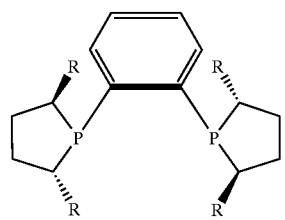

wherein R is alkyl.

4. A method according to claim 3, wherein the chiral catalyst is [Rh(ligand)(COD)]BF$_4$.

5. A method according to claim 3, wherein R is methyl or ethyl.

6. A method according to claim 1, wherein the alkene is the E isomer or the Z isomer or is a mixture of said E isomer and Z isomer.

7. A method according to claim 1, wherein the cation is an alkali metal or alkaline earth metal.

8. A method according to claim 7, wherein the alkali metal is potassium.

9. A method according to claim 1, wherein the cation is a salt of a primary amine or a salt of secondary amine.

10. A method according to claim 9, wherein the amine is tert-butylamine.

11. A method according to claim 1, which further comprises first converting a carboxylic ester of the formula

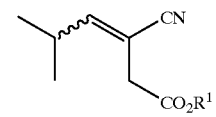

wherein R$^1$ is alkyl, to the carboxylate salt of the formula

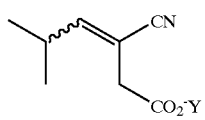

where Y is a cation.

12. A method according to claim 11, wherein $R^1$ is ethyl.

13. A method according to claim 11, wherein the carboxylate salt is isolated prior to hydrogenation.

14. A method according to claim 11, wherein the carboxylate salt is prepared in situ prior to hydrogenation.

15. A method according to claim 1, further comprising acidifying the (S)-3-cyano-5-methylhexanoic acid carboxylate salt to form (S)-3-cyano-5-methylhexanoic acid.

16. A compound of the formula

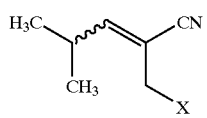

wherein X is $CO_2H$ or $CO_2$—Y, and where Y is a cation.

17. A compound of the formula

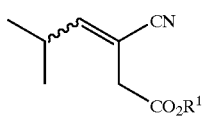

wherein $R^1$ is alkyl.

18. A method for preparing a compound of the formula

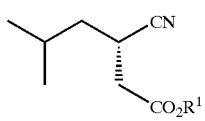

wherein $R^1$ is alkyl, the method comprising asymmetric catalytic hydrogenation of an alkene of the formula

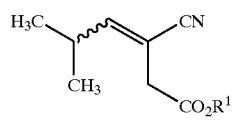

in the presence of a chiral catalyst and a solvent, wherein the chiral catalyst comprises a chiral phosphine ligand.

19. A method according to claim 18, wherein the chiral catalyst is a rhodium complex of an (S,S)-DuPHOS ligand, the ligand having the formula

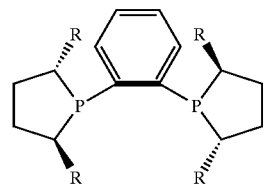

wherein R is alkyl.

20. A method according to claim 19, wherein the chiral catalyst is [Rh(ligand)(COD)]$BF_4$.

21. A method according to claim 19, wherein R is methyl or ethyl.

22. A method according to claim 21, wherein $R^1$ is ethyl.

23. A method according to claim 1, wherein the cation Y is selected from the group consisting of $H^+$, the salt formed by reaction with a protonated primary or secondary amine, an alkaline earth metal, and an alkali metal.

24. A compound of the formula

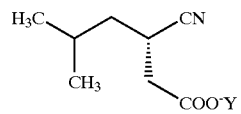

wherein Y is a cation.

25. A method according to claim 1, which further comprises the reduction of the cyano group to form an amino group, and when Y is other than $H^+$, protonation by reaction with an acid to produce pregabalin.

26. A process for preparing pregabalin comprising asymmetrically hydrogenating

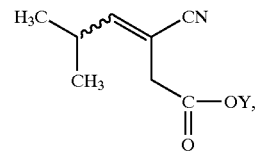

where Y is a cation, in the presence of a chiral catalyst and a solvent, followed by reduction of the cyano group, and protonation to the free acid, wherein the chiral catalyst comprises a chiral phosphine ligand.

* * * * *